United States Patent [19]

Silveston

[11] Patent Number: 4,999,514
[45] Date of Patent: Mar. 12, 1991

[54] TURBIDITY METER WITH PARAMETER SELECTION AND WEIGHTING

[75] Inventor: Peter L. Silveston, Waterloo, Canada

[73] Assignee: Claritek Instruments Inc., Toronto, Canada

[21] Appl. No.: 414,609

[22] Filed: Sep. 28, 1989

[30] Foreign Application Priority Data

Sep. 30, 1988 [CA] Canada ................................. 579077

[51] Int. Cl.[5] ........................................... G01N 15/06
[52] U.S. Cl. .................................... 250/575; 356/343
[58] Field of Search ................ 250/574, 575; 356/336, 356/338–343, 441, 442

[56] References Cited

U.S. PATENT DOCUMENTS

| | | | |
|---|---|---|---|
| 3,694,092 | 9/1972 | Hashimoto et al. | 250/575 |
| 4,180,331 | 12/1979 | Lundstrom | 250/574 |
| 4,201,471 | 5/1980 | Pitt et al. | 356/70 |
| 4,265,535 | 5/1981 | Pitt | 250/575 |
| 4,318,180 | 3/1982 | Lundqvist et al. | 356/442 |
| 4,759,631 | 7/1988 | Sunstein | 250/575 |

Primary Examiner—David C. Nelms
Attorney, Agent, or Firm—Ridout & Maybee

[57] ABSTRACT

A turbidity meter has a sensor unit supported in a fluid under test with a light source and at least two light sensors supported so that one light sensor is in line with the source to receive transmitted light and the remaining sensor or sensors are arranged to receive light scattered by the fluid. Both the source and the sensors have flow forming chambers connected to a source of pressurized fluid so that a thin layer of this fluid is caused to flow over lenses of the source and sensors to prevent deposition of material from the fluid under test. The signals from the sensors are digitized, and the intensity of the source is digitally controlled to maintain at least one of sensor signals within a suitable range, thus enabling operation over a wide range of turbidities, and automatic selection of turbidimetric and nephelometric modes of operation as appropriate.

15 Claims, 3 Drawing Sheets

TURBIDITY METER WITH PARAMETER SELECTION AND WEIGHTING

COPYRIGHT AUTHORISATION

A portion of the disclosure of this patent document contains material which is the subject of copyright protection. The copyright owner has no objection to the facsimile production by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to turbidity meters for the measurement of solids suspended or colour bodies dissolved in a fluid.

2. Review of the Art

Whilst the term turbidity strictly speaking refers to the light transmission and scattering properties of a liquid containing suspended solids, similar techniques to those used for measuring turbidity may commonly be used for determining the degree of opacity of coloured liquids and of gases containing suspended solid or liquid particles. For convenience, the term turbidity will be utilized hereinafter in a broad sense to refer collectively to all of these phenomena unless otherwise indicated.

Whilst direct measurements of turbidity of a fluid can be made by separating the turbidifying phase from the fluid and measuring the weight of both phases separately, this is time consuming and difficult. For most purposes, measurement of the optical properties of the turbid fluid provides a more convenient although indirect way of quantifying turbidity. Commonly measured properties for this purpose are the attenuation and scattering of light passed through the fluid. Measurements of scattering (nephelometry) are usually most suitable when the degree of turbidity and thus attenuation is low, whilst measurements of attenuation (turbidimetry) are most useful when the degree of turbidity and thus attenuation is high. The measurement range of most existing instruments is limited, so that no single instrument can provide a capability extending over the full range of turbidities likely to be encountered in the field.

A further problem arises in instruments having measuring heads which must be submerged in the fluid under test, since material from the fluid or biological growth engendered by the fluid will tend to deposit on windows or lenses associated with light sources and detectors incorporated in the head, thus introducing measurement errors. In instruments that make measurements within the fluid, rather than withdrawing samples for analysis, further errors arise through spurious responses of the light detectors as a result of ambient light.

Instruments currently available are calibrated in turbidity units (Jackson T.V. or N.T.V.) which are based on a standard suspension with reproducible optical properties which are not simply related to the content of suspended solids. The presence of colour due to dissolved solids is interpreted by most current instruments as turbidity. Such instruments are adjusted manually, and measurements are also taken manually or from chart records. Manual adjustments and readings at a measurement location are inconvenient at best and possibly hazardous or impossible: remote operation would be desirable.

SUMMARY OF THE INVENTION

We have sought to address these problems and provide an instrument which can be constructed to provide measurements over a very wide range of turbidities, and which can prevent or reduce to deposition of material on its light sensors and sources exposed to a fluid under test. The instrument can be calibrated at a measuring location, can allow for fluid colour and stray light, and can be controlled and read remotely.

According to the invention a turbidity meter comprises:

(a) a light source, and a lens for focusing light from the source into a beam;

(b) a first light detector producing an output signal responsive to the intensity of light incident thereon;

(c) at least one second light detector producing an output signal responsive to the intensity of light incident thereon;

(d) means supporting said first and second light detectors in defined positions relative to the light source in a fluid under test such that said beam is directed through said fluid towards said first light detector, and each said second light detector is positioned to detect light scattered by said fluid at a predetermined angle to said beam;

(e) means to determine when the amplitude of at least one of the output signals obtained lies within a given range;

(f) means responsive to said determining means to change at least one parameter selected from the intensity of the light source, the effective sensitivity of at least one of the detectors, and the output signal chosen so that the output of at least one of said detectors falls within said range; and (g) means responsive to the altered value of said at least one parameter and the identity of said at least one detector to provide an output signal weighted in accordance with the altered value of said at least one parameter.

The invention also extends to a turbidity meter comprising:

(a) a light source, and a lens for focusing light from the source into a beam;

(b) at least one light detector having a lens and producing an output signal responsive to the intensity of light incident thereon through the lens;

(c) means supporting the lens of each said light detector in a defined position relative to the lens of the light source in a fluid under test such that said beam is directed through said fluid, and each said light detector is positioned to detect light from said beam after one of transmission and scattering by said fluid;

(d) means processing output signals of said at least one detector to provide a signal indicative of the turbidity of the fluid; and (e) means to prevent deposition of material upon the lenses of said source and each said detector;

wherein said means to prevent deposition upon the lenses comprise a source of pressurised fluid compatible with that under test, a flow forming chamber adjacent to each lens and conduits from said source to each said flow forming chambers, each flow forming chamber having an exit orifice partially surrounding the periphery of a surface of its associated lens nearest the fluid under test, whereby a flow of said compatible fluid is maintained over that surface of the lens.

Further features of the invention will become apparent from the following description of a preferred embodiment thereof.

SHORT DESCRIPTION OF THE DRAWINGS

DESCRIPTION OF THE PREFERRED EMBODIMENTS

Figure 1:
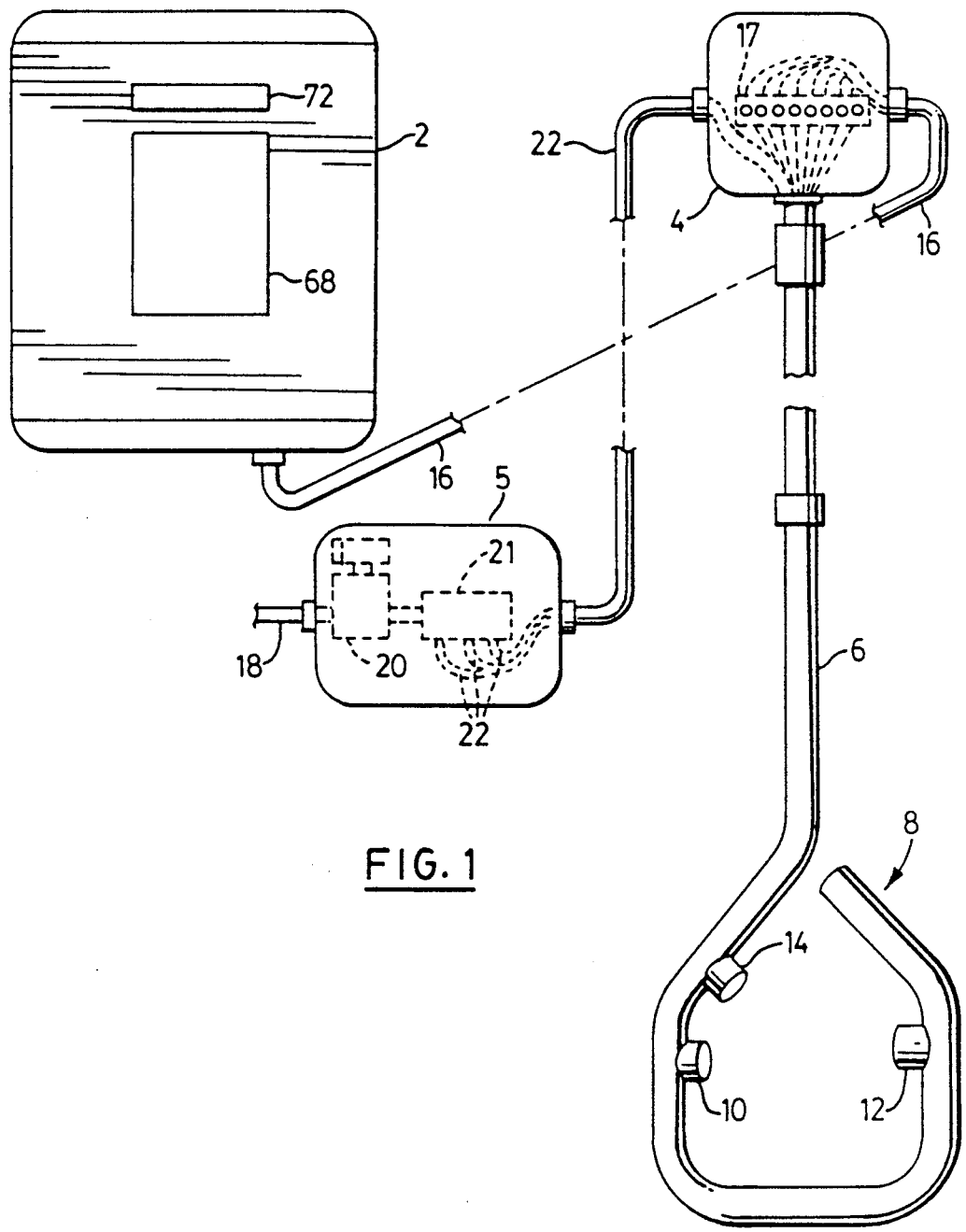
FIG. 1 is an elevational view of an instrument embodying the invention.

Referring to FIG. 1, the instrument consists of a control unit 2, a first junction box 4, a second junction box 5, a rigid tubular corrosion resistant support conduit 6, and a sensor head 8. The sensor head is conveniently a continuation of the support conduit 6, and supports a light source assembly 10 and two sensor assemblies 12, 14 for immersion in the fluid under test, which will usually but not necessarily be a liquid, typically water, containing suspended matter.

The junction box 4 establishes electrical connections through a cable 16 from the control unit 2 to the assemblies 10, 12, 14 by means of a connection block 17. It also passes a group of three tubes 22 extending from the junction box 5 to the assemblies 10, 12 and 14. The junction box 5 has a pressurized fluid supply pipe 18, typically connected to a piped water supply. A regulator valve 20 meters fluid from the pressurized supply through a manifold 21, which may include a pressure sensor 86 (see FIG. 4), to the tubes 22 which pass down the conduit 6 to the assemblies 10, 12, 14.

Figure 2:
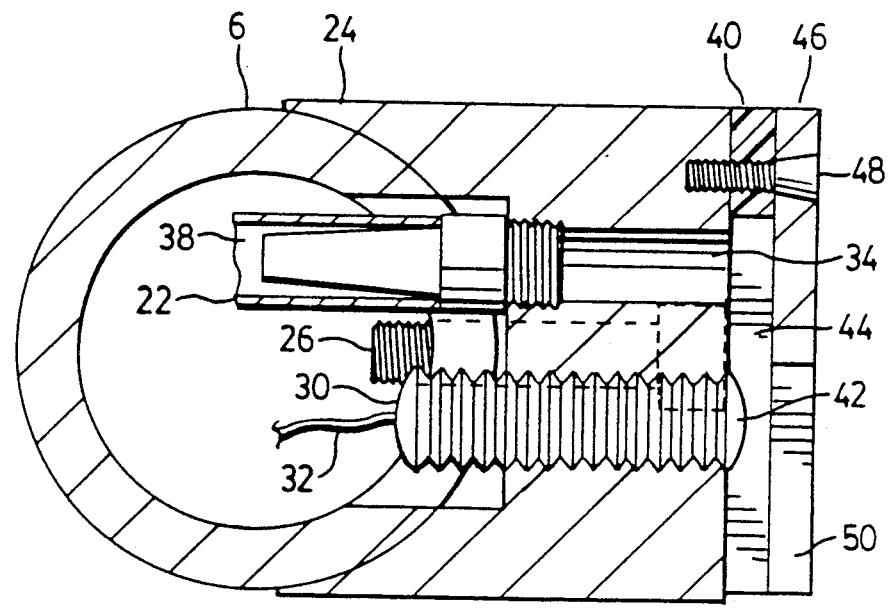
FIG. 2 is a longitudinal cross section of a light source or sensor assembly utilized in the instrument of FIG. 1.
Figure 3:
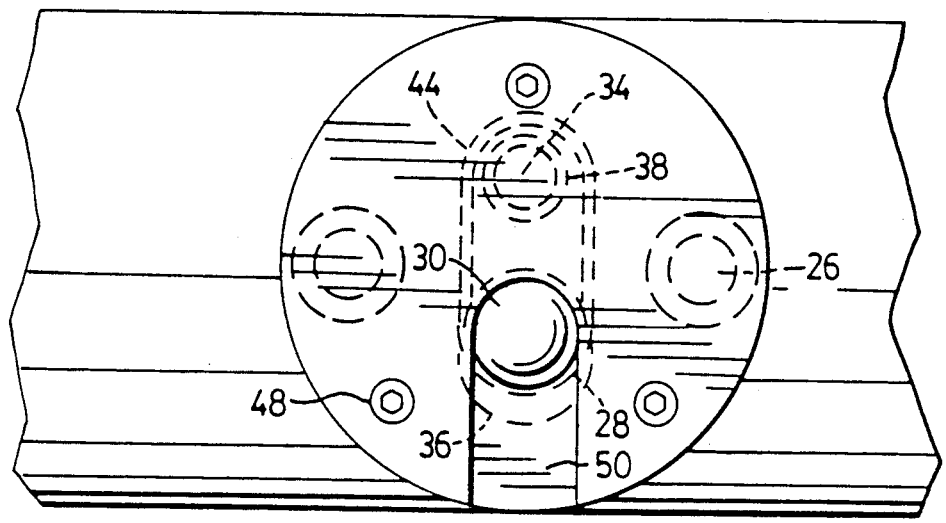
FIG. 3 is an end view of the assembly shown in FIG. 2.

The assemblies 10, 12 and 14 are physically identical, an exemplary assembly being shown in FIGS. 2 and 3. Each has a body 24 secured over a slot 36 in the conduit 6 by screws 26, a watertight seal between the assembly and the body being assured by use of a silicone sealant. The body has a first bore 28 housing an optoelectronic device 30 having connections through a cable 32 to the cable 16 via the terminal block 17. A further parallel bore 34 is fitted with a spigot 38 connected to one of the pipes 22. A washer or gasket 40 has a slot extending over most of its diameter from one side of the assembly, over a lens 42 of the device 30, with the distal portion of the slot forming a flow forming chamber 44 at the outlet of the bore 34. A cover piece 46 is secured over the washer 40 by screws 48, and is also formed with a radial slot 50 overlying the slot in the washer 40 except in the region of the flow forming chamber 44.

The assembly 10 is supported directly opposite and in axial alignment with the assembly 12 (see FIG. 1) so that a beam of light emitted by the device 30 of the assembly 10 and focused by its lens 42 is directed onto the lens 42 and device 30 of the assembly 12.

In preferred arrangement, the device 30 of the assembly 10 is a light emitting diode (LED) of suitable spectral characteristics, whilst the device 30 in each assembly 12 and 14 is a phototransistor which conducts a current proportional to the intensity of light incident upon it. The phototransistors are matched to the light emitting diode of assembly 10 such that they respond to light of similar spectral characteristics to that emitted by the diode. By suitable choice of the diode and transistors, a fairly high degree of immunity to ambient light conditions can be obtained. Typically gallium arsenide diodes are used which emit monochromatic light in the infra red region at 940 nm. It should be understood however that other light sources such as incandescent lamps or solid state lasers, and other sensor devices such as photodiodes and bolometers can be utilized, possibly in conjunction with colour filters or other devices to restrict spectral response in a manner such as to reduce the influence of ambient light. A phototransistor operates over a very wide range of currents, and as such its effective sensitivity can be adjusted by modifying the gain of preamplifiers 54 and 56 (see FIG. 4).

The assembly 14 is disposed so that the optical axis of the system formed by its LED 30 and associated lens 42 intersects the common axis of the assemblies 10, and 12 at an angle of 45° so as to receive light scattered rearwardly at that angle from the beam generated by the assembly 10. Whilst the exemplary embodiment shown is arranged so that the assembly 14 receives light scattered rearwardly at an angle of 45°, the position of the assembly can be changed so that it is disposed to receive light scattered at different angles, or so that it receives forwardly scattered light. Alternatively, additional assemblies 14 may be provided having different angular relationships to the source. The assembly 14 may be mounted at the bottom of the head rather than in the position shown.

The LED in the assembly 10 is connected by the cables 32 and 16 to a current source 52 (see FIG. 4) in the control box 2, whilst the phototransistors in the assemblies 12 and 14 are similarly connected to preamplifiers 54 and 56 respectively. Whilst these preamplifiers will usually be located in the control unit 2, they may be located in the connection box 4 or at the assemblies 12 and 14, particularly if a long cable 16 is required. The preamplifiers act in fact as current to voltage converters. At least the preamplifier 54 has a plurality of selectable levels of gain, the value of resistance in a negative feedback path of the amplifier being selected by means of a multiplexer 78 which decodes a digital input signal to switch different resistances or combinations of resistances into the feedback path.

Figure 4:
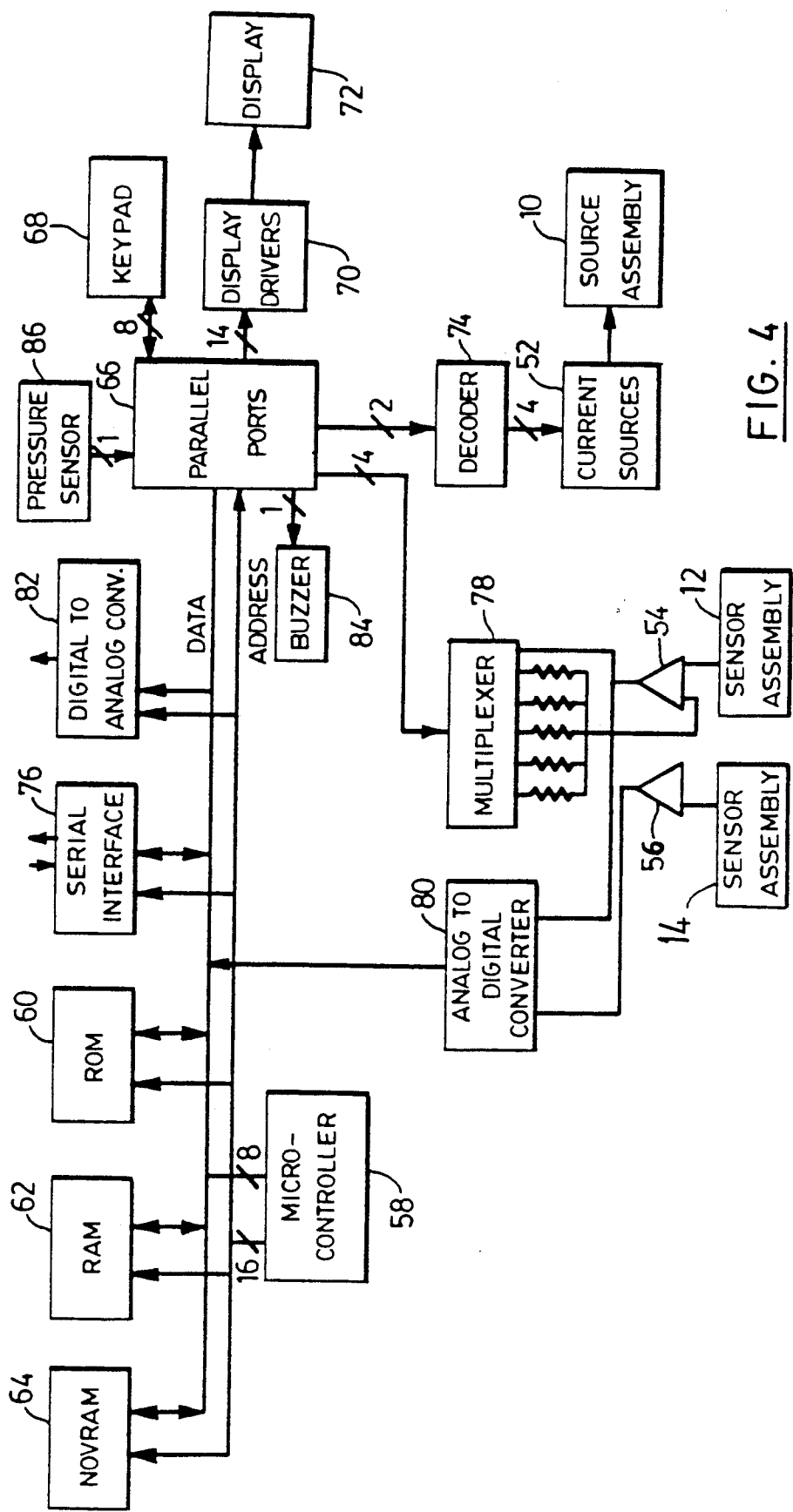
FIG. 4 is a block schematic diagram of electronic components of the instrument.

The internal circuitry of the control unit 2 is described further with reference to FIG. 4. The instrument is under control of a microcontroller 58, which is conveniently of type 8052AH-BASIC from Intel Corporation. This controller includes an eight bit microprocessor, various peripherals and a dialect of the Basic language resident internally in read only memory so that the microcontroller can be programmed directly in BASIC; the BASIC program in this case is stored in a read only memory 60.

The controller is also provided with random access memory, including both volatile memory 62 and nonvolatile memory 64, the former being utilized as working memory and the latter for the storage of instrument readings and parameters required on a longer term basis.

Parallel ports 66 are provided both by the built-in ports of the controller 58 and an external parallel port unit 66, conveniently of type 8255 from Intel Corporation. The ports 66 provide an interface between the controller 58 and a keypad 68 through which data and commands may be entered into the system. They also provide, through drivers 70, an interface with a display 72, typically consisting of a sixteen digit LCD display and several individual indicator LEDs. A control line is also provided to a piezoelectric buzzer 84 to provide audible feedback to a user. Lines from the parallel port unit are connected to the multiplexer 78 to vary the gain of preamplifier 54, and/or to a decoder 74 to provide one of four selection of four different currents which can be generated by the current source 52, which would in that case consist of four current sources with their outputs connected in parallel and inputs switched by field effect transistors connected via suitable drivers to the decoder outputs. An input line may also be provided from the pressure sensor 86, which would be monitored by the controller to verify the existence of adequate fluid pressure in the tubes 22, failing which an alarm output to the buzzer 84 and other outputs of the instrument would be provided. In the description that follows, a simplified arrangement is described in which only the gain of the preamplifier 54 is controlled, the current from current source 52 remaining constant and merely being turned on or off by the port unit 66.

A digital-to-analog converter 82 provides output data from the controller in analog form for use by an external process controller or alarm device, and preferably includes an output circuit providing a standard 4–20 ma output.

The controller is also connected to a serial interface 76 providing a serial port conforming with an accepted standard such as RS232C so that it may interchange data with a remote computer. Depending on requirements, this may be implemented externally, but a presently preferred embodiment uses internal serial ports of the controller with suitable external drivers.

The preamplifiers 54 and 56, and corresponding preamplifiers for any additional sensors which may be provided, are connected to the inputs of multiple channel analog to digital converter 80 whose digital outputs are available to the data bus of the controller 58 on demand.

The controller 58 incorporates a clock generator conventionally frequency stabilized by a quartz crystal, and a built-in real time clock and real time interrupt system. Further features of the controller 58 can be found in the relevant product literature published by Intel Corporation.

The ports incorporated in the interface 66, the serial interface 76, the LCD display, the multiplexer 78 and the analog to digital converter 80 are all mapped into the memory space of the controller 88.

It will of course be understood that the control unit 2 is provided with a suitable electrical power supply, either line or battery operated.

In use of the apparatus, the sensor head 8 is supported so that it is submerged in a fluid under test. It is assumed for the purposes of description that this is an aqueous liquid. The pipe 18 is connected to a piped water supply which in general will provide sufficient pressure to provide a desired flow through the apparatus. The regulator valve 20 is set to provide a flow through the pipes 22 such that water will leave the flow forming chambers 44 and pass across the lenses 42 at a flow rate preferably in the range of 0.5 to 2.0 cm/s. The pressure sensor 86, if provided, verifies that adequate pressure is available. Typically the height of each chamber 44, as determined by the thickness of the washer or gasket 40, is about 0.8 mm. The extent of the chamber, between the passage 34 and the exit from the chamber around one half of the periphery of the lens 42, is sufficient to produce a substantially uniform generally laminar flow from the flow forming chamber across the surface of the lens and out through the slot 50. Other arrangements of flow forming chamber may be employed that will achieve the same result, i.e. a curtain-like flow over the lens that will prevent deposition of material from the fluid under test. The small quantity of clean water introduced into the fluid under test will be insufficient to have any significant effect upon the turbidity readings obtained.

A known approach to preventing unwanted deposition on sensor or light source lenses has been to provide a ring of pressurized liquid jets surrounding the lens and parallel to its axis. The axis of the jets may be yawed from the axis of the lens to impart a slight swirl to the liquid. Such an arrangement however provides a greater interference with fluid under test in the path of light entering or leaving the lens than does the relatively thin laminar flow of the present arrangement, and is likely to require the use of greater quantities of a pressurized fluid.

In the example described, the pressurized fluid is water. Where the fluid under test is not aqueous, the pressurized fluid should be compatible with the fluid under test. If a pressure pump is provided, a part of the fluid under test may be pressurized and utilized, although in this case a filter should be provided to remove suspended matter from the fluid so utilized.

Whilst in the arrangement described, the lenses 42 would be directly exposed to the fluid under test were it not for the flow of pressurized fluid discussed above, in other arrangements the light source or sensors might be located behind windows. The term lens, as used here and in the appended claims should be read as including such windows or any other transparent layer through which light passes between the source or sensors and the fluid under test. The fluid flow from the flow forming chamber should be at least wide enough to cover the effective area of the lens, and preferably somewhat wider.

Once the sensor head 8 is installed and the regulator valve 20 is adjusted, the control unit 2 is powered up and the program stored in ROM 60 commences to execute. The program first initializes various storage arrays in RAM 62, sets up default values of variables used during operation, including variables indicating the addresses for the display, the analog to digital converter, the serial port and the ports provided by unit 66. It then sets up a record buffer in NOVRAM 64 for storage of data captured by the unit during use, and initializes the real time clock.

The system is next tuned for each possible source-detector combination. This involves activating the source assembly and selecting in turn each value of gain provided by the preamplifier 54, by means of the multiplexer 78, in order to determine which gain level is best suited for maintaining the output of preamplifier 54 within a preferred range. For each level of gain the outputs of preamplifiers 54 and 56 are sampled first with the LED source in assembly 10 turned on, and secondly with it turned off, the second samples being subtracted from the first so as to reduce the effect of ambient light. The preamplifier outputs are sampled by the A/D converter 80. In practice a set of 1–200 sets samples taken at intervals is obtained for each level of gain, and for each selection of sensor assembly, and each set of readings obtained is averaged. The averaged readings are reviewed to determine the most appropriate source-sensor pair to select for use, and the most appropriate gain to select for the amplifier 54 associated with assembly 12. If the current applied to the LED in assembly 10 is selectable, the effect of different current levels can be similarly tested.

Assuming that the maximum digitized signal level which can be handled by the converter 80 is 255, this signal level is subtracted from a value representing approximately the midpoint of the signal range, for example 128, and the result is squared, thus producing an output which increases according to the divergence of the reading from the mid point of the range. The most appropriate value gain to select is that which minimizes the output, i.e. which produces a signal level nearest the middle of the range. In fluids of low turbidity, each of the gain values will result in a signal from the sensor assembly 12 which saturates the converter 80 and thus this signal will have no influence upon the selection process, which will then select the sensor assembly 14.

Once the source detector pair and the gain value for the preamplifier 54 have been initially selected, the program enters a loop in which direct or scattered light readings from the sensors are taken at intervals determined by the real time clock and averaged, the averaged readings being compared with previous readings. If the new averaged reading is outside a defined range, then the tuning process described above is repeated, and a new set of readings is then taken and averaged. Otherwise the averaged readings are subjected to further processing by a data smoothing algorithm and undergo appropriate logarithmic transformation prior to display to allow for the gain value selected, and to allow for whether the signals selected are those from the sensor assembly 12 or the sensor assembly 14 (in some cases both).

The output may be fitted to a calibration curve so as to convert it to desired units for the purpose of display, or the data can be displayed in raw form. The calibration curve may for example translate the readings into J.T.V. or N.T.V. units, grains/ft$^3$ or mg/L. In the example program provided in the appendix, this is achieved by applying a linear equation to the transformed signals to generate data in the desired units. Constants for use in the equation are supplied to the control unit either via the serial port or the keyboard. The data may be displayed directly by the control unit 2, and/or transmitted via the serial interface to a printer for printing or to another computer for further processing. Successive readings are stored in NOVRAM 64 so that they may be dumped or reviewed as required, and will be retained even when the instrument is powered down.

Successive raw readings are taken in sets which are averaged as described above before further processing. Provision can be made for readings which differ widely from immediately preceding readings to be rejected unless repeated several times; this enables erratic readings due to such phenomena as bubbles in the fluid to be rejected, and avoids output jitter.

It will be understood that various modifications to the arrangement described are possible, some of which have already been mentioned above. Thus whilst in the embodiment described, automatic range switching or 'tuning' of the apparatus is performed by switching the gain of a preamplifier in a sensor, additional or alternative range switching can be implemented by changing the current applied to the LED in assembly 10. Mechanical means of range switching may also be employed, for example by physically moving the source and sensors towards or away from each other, or by applying iris arrangements to change the effective aperture of the lenses of the source and/or sensor assemblies.

In the arrangement described above, the apparatus by default preferentially uses the turbidometric mode of operation, the source-sensor pair provided by the assemblies 10 and 12 being selected if a suitable signal level can be obtained, with fall back to the nephelometric mode using assemblies 10 and 14 when turbidity is too low to provide usable signal levels in the turbidometric mode. Other forms of operation are possible. Thus in some cases it may be desired to disable either the nephelometric or the turbidometric mode, or to utilize data from both in combination. With suitable programming of the unit, the operating format can be selected either from the keyboard or by an external computer or control unit communicating with the control unit 2 through its serial port.

The NOVRAM 64 permits the instrument to serve as a monitor over an extended time period. In this mode, turbidity data readings are stored, together with a time from the real time clock, only when a change occurs, and sampling intervals are selected according the period over which monitoring is required and according to the memory available. In a typical configuration, about 1000 readings may be stored before early readings are overwritten; more extended periods of operation can be achieved by periodic dumping of data to an external printer or a host computer. The instrument can be utilized for process control or alarm purposes by use either of the analog output from the digital-to-analog converter 82, which may be provided with a standard 4-20 ma interface, or of digital data from the serial interface 76, each of which can provide the running average output signal discussed above. The use of the averaged signal provides some protection against erroneous readings produced by gas bubbles and the like, thus reducing the risk of false alarms.

Since the preferred form of the invention utilizes a light source producing monochromatic light, typically in the infra-red region, a correction is necessary to allow for changes in the apparent turbidity of the fluid under test as compared to observations made using visible light of conventional spectral distribution. Such correction, if required, can be incorporated in calibration data provided to the control unit.

Provision may also be made to compensate for ambient light by periodically determining the output of the sensor assemblies when the source assembly is turned off, so as to provide a correction to be applied to the readings. This technique has already been described above in connection with the tuning procedure. Any compensation necessary for stray light from the source, for example reflected from the walls of a vessel within which measurements are made, can be applied as part of the calibration data. Similarly, allowance for colour background can be made utilizing data from both the sensors 12 and 14 in conjunction with a mathematical model of the scattering phenomenon. Allowance for background can also be made during calibration.

The following Appendix represents the presently preferred version of the program stored in ROM 60, to which reference is made above. Copyright in this program is owned by Claritek Instruments Inc.

```
REM ********************************************************************
REM This program, written in MCS BASIC-52, is designed for the CLARITEK  *
REM SM8830 Suspended Solids Monitor.  The program is stored on a 16Kbyte *
REM EPROM located on-board the BCC-52 Computer/Controller, and is        *
REM automatically executed on power-up or reset.                         *
REM                                                                      *
REM                           ** V1.0 **                                 *
REM                                                                      *
REM ********************************************************************
REM
REM (MAIN) - CHANGES SD, TMNEX
REM          USES SDMAX, RCAL REM initialize storage arrays
50 STRING 35,16
55 DIM K1(3),K2(3),K3(3),GAIN(3),SU(3),SL(3)
57 DIM KS1(3),KS2(3),KS3(3),SSU(3),SSL(3)
60 DIM ADADDR(7),KPD(15),WINST(3),WR(3)
65 DIM MAXPTS(3),ALPHA(27)

REM initialization of ALL variables and data structures.
90  CLEARS:GOSUB 5840:PF=XBY(MEMMAX):IF PF=1 THEN GOSUB 500
100 TIME=0:CLOCK1

REM tune-system for each source detector set
140 FOR SD=0 TO SDMAX:GOSUB 750:NEXT SD:SD=0

REM If we are restarting after a power interruption, skip the Main Menu
REM and proceed directly to the run mode.
160 IF PF=0 THEN GOSUB 2940

REM Set up polling routine.
170 TMNEX=TIME+2:ONTIME TMNEX,890

REM The following lines are continuously executed during
REM operation of the system.

REM Loop on detectors, get-avg-light-readings
280 FOR SD=0 TO SDMAX:CLEARI:GOSUB 400:GOSUB 590

REM If the sample goes out of bounds tune the system.
350 IF AVGS<0 THEN AVGS=0
351 IF AVGD<0 THEN AVGD=0
352 IF AVGDN<0 THEN AVGDN=0
353 IF AVGDFF<0 THEN AVGDFF=0
360 IF (AVGDN>250).OR.((AVGDN-AVGDFF)<15) THEN GOSUB 750
375 IF TMNEX < (TIME+.1) THEN TMNEX=TIME+1
376 ONTIME TMNEX,890

REM Get average, calculate values, print results, next action
379 GOSUB 1760:GOSUB 2080
380 ON (DISP-1) GOTO 381,382,383,384,385,386,387,388,389
381 PUSH RCAL:GOTO 390
382 PUSH TCAL:GOTO 390
383 PUSH AVGD:GOTO 390
384 PUSH AVGDN:GOTO 390
385 PUSH AVGDFF:GOTO 390
386 PUSH GAIN(SD):GOTO 390
387 PUSH RSCAL:GOTO 390
388 PUSH TSCAL:GOTO 390
389 PUSH AVGS
390 GOSUB 1380:GOSUB 1430:IF (DISP<=2.OR.DISP=7.OR.DISP=8) THEN GOSUB 1740
395 GOSUB 570:NEXT SD:GOTO 280

REM (CRITICAL DATA STORAGE) - CHANGES
REM                         - USES
```

```
400 PUSH I,J,K:I=MEMMAX:XBY(I)=1:XBY(I+1)=INT(SYR/100)
402 XBY(I+2)=SYR-100*(INT(SYR/100)):XBY(I+3)=SMTH:XBY(I+4)=SDAY
404 XBY(I+5)=SHRS:XBY(I+6)=HRSL:XBY(I+7)=HRSH:XBY(I+8)=SDMAX:XBY(I+9)=WRAPS
406 XBY(I+10)=RAW:XBY(I+11)=DISP:XBY(I+12)=DISPU
408 PUSH DELTA,NXTREC,NRRECS,NXTBITE:ST@ I+18:ST@ I+24:ST@ I+30:ST@ I+36
410 I=I+36:FOR J=0 TO 3:K=I+J*61:PUSH SSU(J),SSL(J),KS3(J),KS2(J),KS1(J)
412 PUSH SU(J),SL(J),K3(J),K2(J),K1(J):ST@ K+6:ST@ K+12:ST@ K+18:ST@ K+24
414 ST@ K+30:ST@ K+36:ST@ K+42:ST@ K+48:ST@ K+54:ST@ K+60
416 XBY(K+61)=MAXPTS(J):NEXT J:POP K,J,I:RETURN

REM (CRITICAL DATA RETRIEVAL) - CHANGES
REM                            - USES

500 PUSH I,J,K:I=MEMMAX:PF=XBY(I):SYR=100*XBY(I+1)+XBY(I+2):SMTH=XBY(I+3)
502 SDAY=XBY(I+4):SHRS=XBY(I+5):HRSL=XBY(I+6):HRSH=XBY(I+7):SDMAX=XBY(I+8)
504 WRAPS=XBY(I+9):RAW=XBY(I+10):DISP=XBY(I+11):DISPU=XBY(I+12):LD@ I+18
506 LD@ I+24:LD@ I+30:LD@ I+36:POP DELTA,NXTREC,NRRECS,NXTBITE:I=I+36
508 FOR J=0 TO 3:K=I+J*61:LD@ K+6:LD@ K+12:LD@ K+18:LD@ K+24:LD@ K+30
510 LD@ K+36:LD@ K+42:LD@ K+48:LD@ K+54:LD@ K+60:POP SSU(J),SSL(J),KS3(J)
512 POP KS2(J),KS1(J),SU(J),SL(J),K3(J),K2(J),K1(J):MAXPTS(J)=XBY(K+61)
514 NEXT J:POP K,J,I:RETURN

REM (PAUSE BETWEEN MEAN SAMPLES) - CHANGES
REM                               - USES LARGEINC

570 FOR I=1 TO LARGEINC:NEXT I
575 RETURN

REM (GETAVGRDING) - CHANGES AVGD, AVGS, DAD, SAD, I, TMNEX
REM               - USES ADADDR, SD, SMALLINC

590 AVGD=0:AVGS=0:DAD=ADADDR(SD):SAD=ADADDR(SD+4):I=0
595 AVGDN=0:AVGDFF=0:AVGS1=0:AVGS0=0
597 XBY(BPORT2)=GAIN(SD)+7
600 GOSUB 670:RD=XBY(DAD):RS=XBY(SAD)
605 AVGDN=AVGDN+(RD/20):AVGS1=AVGS1+(RS/20)
610 GOSUB 720:RD=RD-XBY(DAD):RS=RS-XBY(SAD)
615 AVGDFF=AVGDFF+(XBY(DAD)/20):AVGS0=AVGS0+(XBY(SAD)/20)
620 AVGS=AVGS+RS/20:AVGD=AVGD+RD/20:I=I+1:IF I=20 THEN 650
630 TMNEX=TIME+SMALLINC
640 IF TIME > TMNEX THEN 600 ELSE 640
650 RETURN

REM (LIGHTSON)    - CHANGES
REM               - USES APORT2, BPORT2, SD, GAIN

670 XBY(APORT2) = 8:RETURN

REM (LIGHTSOFF) - CHANGES
REM             - USES APORT2,

720 XBY(APORT2)=0:RETURN

REM (TUNESYSTEM) - CHANGES BESTRD, GAIN, BESTI, RD
REM              - USES SD, AVGD, AVGS

750 $(1)=" Tuning":PUSH 7:GOSUB 1410:PUSH SD+1:GOSUB 1430
770 BESTRD = (128**2) + 1:GAIN(SD)=1:BESTI= 1
780 REM get-average-readings()
790 GOSUB 590:RD = (128-AVGD)**2
825 IF (AVGDN>250).OR.((AVGDN-AVGDFF)<15) THEN 840
830 IF RD < BESTRD THEN BESTRD = RD: BESTI = GAIN(SD)
```

```
840 GAIN(SD) = GAIN(SD) + 1:IF GAIN(SD) <= 8 THEN 790
850 GAIN(SD) = BESTI:GOSUB 1755:GOSUB 590:RETURN

REM (POLLINTERRUPT) - CHANGES HRSL, HRSH, KEYIN, TMNEX, SD
REM                 - USES I, CH, PASSWD

890 PUSH SD,I,J:IF TIME < HOUR THEN 980
940 I=INT(TIME/HOUR):TIME=TIME-I*HOUR
950 HRSL=HRSL+I:IF HRSL < 255 THEN 980
960 J=INT(HRSL/255):HRSL=HRSL-J*255:HRSH=HRSH+J
REM poll-keyboard
980 SD=0:IF GET = 48 THEN KEYIN = 0: GOTO 1050
REM poll-keypad
1000 GOSUB 2640:POP CH: IF CH = 48 THEN KEYIN = 1: GOTO 1050
1002 IF (CH>=1).AND.(CH<=5) THEN DISP=CH
1006 IF CH=13 THEN DISP=6
1007 IF CH=49 THEN DISP=7
1008 IF CH=50 THEN DISP=8
1009 IF CH=51 THEN DISP=9
1030 GOTO 1080
REM get-password()
1050 GOSUB 1600:GOSUB 2730:POP PASSWD
REM get-user-input()
1070 IF PASSWD = 1 THEN GOSUB 2940
1080 TMNEX=TIME+1:ONTIME TMNEX,890:POP J,I,SD:RETI
REM (CLEARSCRN) - CHANGES RESETS SCREEN
REM             - USES PORTA

1380 XBY(PORTA)=1:XBY(PORTA)=0EH:XBY(PORTA)=6:XBY(PORTA)=38H:E2=0:RETURN

REM (CHECK IF EIGHTH LCD DIGIT REACHED) - CHANGES
REM                                     - USES E2, PORTA

1390 IF (E2=8) THEN XBY(PORTA)=0C0H
1395 RETURN

REM (PRINT STRING TO LCD) - CHANGES I, J
REM                       - USES PORTA, PORTB, E2

1400 POP J:PUSH I:FOR I=1 TO J
1405 XBY(PORTB)=ASC($(1),I):E2=E2+1:GOSUB 1390:NEXT I:POP I:RETURN

REM (CLEAR LCD AND PRINT STRING) - CHANGES
REM                              - USES

1410 GOSUB 1380:GOSUB 1400:RETURN

REM (SETLCDVALUE) - CHANGES
REM               - USES PORTB
REM  Note that this code assumes that LCDNUM is less then 1000000.

1430 POP LCDNUM:PUSH I,J,E:IF ABS(LCDNUM)>=(10**6) THEN GOSUB 1640:GOTO 1520
1440 IF LCDNUM<0 THEN XBY(PORTB)=2DH:LCDNUM=ABS(LCDNUM) ELSE XBY(PORTB)=20H
1445 E2=E2+1:GOSUB 1390
1450 NUM=0:E=1:J=2:FOR I=5 TO 0 STEP-1
1460 NUM=INT(LCDNUM/(10**I)):IF (E=1 .AND. NUM=0) THEN 1480
1470 E=0:XBY(PORTB)=NUM+30H:E2=E2+1:LCDNUM=LCDNUM-NUM*(10**I):GOSUB 1390
1480 IF (I=0 .AND. E=1) THEN XBY(PORTB)=30H:E2=E2+1:J=6
1490 NEXT I:GOSUB 1390:XBY(PORTB)=2EH:E2=E2+1:FOR I=1 TO J
1500 GOSUB 1390:NUM=INT(LCDNUM*10):XBY(PORTB)=NUM+30H:E2=E2+1
1510 LCDNUM=LCDNUM*10-NUM:NEXT I:IF (E2<=8) THEN XBY(PORTA)=0C0H:E2=8
1520 POP E,J,I:RETURN
```

REM (LCDTOPSWD?) - USES PORTB

1600 $(1)=" Password?":PUSH 10:GOSUB 1410:RETURN

REM (LCDTOERROR) - CHANGES
REM              - USES PORTB

1640 $(1)=" Error":PUSH 6:GOSUB 1410:GOSUB 2570:RETURN

REM (UNITS=mg/L) - CHANGES
REM              - USES

1655 $(1)=" mg/L":GOSUB 1400:RETURN

REM (UNITS=g/L) - CHANGES
REM             - USES

1660 $(1)="  g/L":GOSUB 1400:RETURN

REM (UNITS=ppm) - CHANGES
REM             - USES

1665 $(1)="  ppm":GOSUB 1400:RETURN

REM (UNITS=%) - CHANGES
REM           - USES

1670 $(1)="    %":GOSUB 1400:RETURN

REM (UNITS=NTU/JTU) - CHANGES
REM                 - USES

1675 IF DISP<=2 THEN $(1)="  JTU" ELSE $(1)="  NTU"
1677 GOSUB 1400:RETURN

REM (DISPLAYUNITS) - CHANGES
REM                - USES

1740 PUSH 5:ON (DISPU-1) GOSUB 1655,1660,1665,1670,1675:RETURN

REM (INPUTSEQ) - CHANGES
REM            - USES

REM DETERMINE LCD DIGITS, PUT THEM, GET INPUT
1750 GOSUB 1430: GOSUB 2360: RETURN

REM (WINCLR) - CHANGES I, POSN, WR
REM          - USES SD, MAXPTS, WINST

1755 PUSH I:POSN=WINST(SD):FOR I=1 TO MAXPTS(SD):XBY(POSN)=0:POSN=POSN+13
1756 NEXT I:POP I:WR(SD)=0:RETURN

REM (WINAVG) - CHANGES NXTBITE, DMEAN, SMEAN, I, WR, OLDD, OLDS
REM          - USES SD, WINST, GAIN, AVGD, AVGS, MAXPTS, DELTA

REM Averaging window calculations
REM A floating point number requires 6 bytes to be stored in memory
REM using the SD@ and LD@ operators.

```
1760 NXTBITE=WINST(SD)+WR(SD)*13:XBY(NXTBITE)=GAIN(SD)
1761 IF AVGD < 0 THEN AVGD = 0
1762 IF AVGS < 0 THEN AVGS = 0
1768 PUSH AVGS:ST@ NXTBITE+6:PUSH AVGD:ST@ NXTBITE+12
1769 WR(SD)=WR(SD)+1:IF WR(SD)=MAXPTS(SD) THEN WR(SD)=0
1770 DMEAN=0:SMEAN=0:NXTBITE=WINST(SD):FOR I=1 TO MAXPTS(SD)
1772 IF(XBY(NXTBITE)=0) THEN 1780
1774 LD@ NXTBITE+12:POP DB:LD@ NXTBITE+6:POP SB
1775 DMEAN=DMEAN+DB:SMEAN=SMEAN+SB
1776 NXTBITE=NXTBITE+13:NEXT I
1780 I=I-1:DMEAN=DMEAN/I:SMEAN=SMEAN/I
1781 IF PF=1 THEN 1783
1782 IF(ABS(OLDD-DMEAN)/(OLDD+.01)) < DELTA THEN 1785
1783 OLDD=DMEAN:OLDS=SMEAN:GOSUB 1790
1785 GOSUB 2280:RETURN

REM (SAVEREC) - CHANGES POSN, NXTREC, WRAPS, NRRECS
REM            - USES MEMSTRT, RECSIZ, SD, GAIN, HRSL, HRSH, SMEAN,
REM                   DMEAN, MAXRECS

REM Note that the "power interrupted" variable
REM "PF" is reset to zero once a record is stored.

1790 POSN = MEMSTRT + (NXTREC*RECSIZ)
1880 XBY(POSN)=(PF*128)+(10*SD)+GAIN(SD):XBY(POSN+1)=HRSH:XBY(POSN+2)=HRSL
1885 IF DMEAN < 0 THEN DMEAN = 0
1886 IF SMEAN < 0 THEN SMEAN = 0
1890 PUSH DMEAN:ST@ POSN+8:PUSH SMEAN:ST@ POSN+14:NXTREC=NXTREC+1
1895 IF NXTREC > MAXRECS THEN NXTREC = 0: WRAPS = WRAPS + 1
1896 IF WRAPS = 0 THEN NRRECS = NRRECS + 1
1897 PF=0:RETURN

REM (GETREC) - CHANGES POSN, HRSH, HRSL, DMEAN, SMEAN, GAIN, SD
REM           - USES RECSIZ, MAXRECS, MEMSTRT

1940 POP POSN
1950 IF (POSN < 0) .OR. (POSN > MAXRECS) THEN P."INVALID NUMBER":RETURN
1960 POSN = MEMSTRT + (POSN*RECSIZ)
1963 PF=(XBY(POSN).AND.128)/128:SD=INT((XBY(POSN)-(PF*128))/10)
1965 GAIN(SD)=XBY(POSN)-(10*SD)-(128*PF):HRSH=XBY(POSN+1)
1970 HRSL=XBY(POSN+2)
1975 LD@ POSN+8:POP DMEAN:LD@ POSN+14:POP SMEAN:RETURN

REM (CALCVALS) - CHANGES ALPH, TMS, TMD, TM, RCAL
REM             - USES SD, GAIN, DMEAN, SMEAN
REM                    K1, K2, K3, DMEAN4 SMEAN4

2080 IF GAIN(SD) = 1 THEN ALPH = 1:GOTO 2112
2090 ALPH=ALPHA(SD*7+GAIN(SD)-2)
2112 IF DMEAN=0 THEN DMEAN=0.0001
2114 IF SMEAN=0 THEN SMEAN=0.0001
2200 IF AVGD=0 THEN AVGD=0.0001
2225 IF AVGS=0 THEN AVGS=0.0001
2230 RCAL = (K1(SD)-LOG(DMEAN/ALPH))/K2(SD)+K3(SD)
2231 TCAL = (K1(SD)-LOG(AVGD/ALPH))/K2(SD)+K3(SD)
2232 RSCAL = (KS1(SD)-LOG(SMEAN))/KS2(SD)+KS3(SD)
2233 TSCAL = (KS1(SD)-LOG(AVGS))/KS2(SD)+KS3(SD)
2235 IF RCAL<0 THEN RCAL=0
2236 IF TCAL<0 THEN TCAL=0
2237 IF RSCAL<0 THEN RSCAL=0
2238 IF TSCAL<0 THEN TSCAL=0
2240 IF DISP>=7 THEN 2260
2243 IF RCAL>SU(SD) THEN XBY(PORTC) = 240:RETURN
2244 IF RCAL<SL(SD) THEN XBY(PORTC)=48:RETURN
2250 XBY(PORTC)=INT(48+(RCAL-SL(SD))/(SU(SD)-SL(SD))*192):RETURN
```

```
2260 IF RSCAL>SSU(SD) THEN XBY(PORTC)=240:RETURN
2262 IF RSCAL<SSL(SD) THEN XBY(PORTC)=48:RETURN
2264 XBY(PORTC)=INT(48+(RSCAL-SSL(SD))/(SSU(SD)-SSL(SD))*192):RETURN

REM (PRINTSAMPLE) - CHANGES
REM               - USES TCAL, SD, GAIN, AVGD, AVGS,
REM                 AVGDN, AVGDFF;TSCAL,AVGSO,AVGS1

2280 P."S/D    Gain       Scattered              Extinction"
2290 P."Set               Susp. Solids/NTU       Susp. Solids/JTU"
2300 P.
2310 P. U.(#), SD+1,
2312 P. U.(#),TAB(8),GAIN(SD),
2314 IF TSCAL>1.0 THEN P. U.(######.##), ELSE P. U.(#.######),
2315 P. TAB(18),TSCAL,TAB(32),:IF DISPU=5 THEN P." N",
2316 GOSUB 2340
2318 IF TCAL>1.0 THEN P. U.(######.##), ELSE P. U.(#.######),
2319 P. TAB(45),TCAL,TAB(59),:IF DISPU=5 THEN P." J",
2320 GOSUB 2340:P. " ":P.
2321 IF RAW=1 THEN P. U.(0),AVGD,AVGS,AVGDN,AVGDFF,AVGS1,AVGSO
2330 P.:P. U.(0):RETURN

REM (PRINTUNITS) - CHANGES
REM              - USES DISPU

2340 ON (DISPU-1) GOTO 2341,2342,2343,2344,2345
2341 P. "mg/L",:RETURN
2342 P. " g/L",:RETURN
2343 P. " ppm",:RETURN
2344 P. "   %",:RETURN
2345 P. "TU",:RETURN

REM (GETINPUT) - CHANGES DP, USN, INFLAG, J
REM            - USES KEYIN, CH

2360 PUSH I,J:DP = 0:NE=1:USN=0: INFLAG=0:P. ">>",
2370 J = 0
2380 IF J< 65535 THEN 2405
2390 USN=TMOUT:IF KEYIN = 0 THEN P. "TIMED OUT ON KEYBOARD":GOTO 2565
2400 P. "TIMED OUT ON KEYPAD INPUT":GOTO 2565

2405 IF(INFLAG<>0) THEN 2410
2406 J=J+1:GOSUB 2600:POP CH:IF CH<>0 THEN KEYIN=0:GOTO 2408
2407 GOSUB 2640:POP CH:IF CH=0 THEN 2380 ELSE KEYIN=1
2408 IF (CH<>13) THEN 2450 ELSE USN = NODIGIT:P. " ":NE=1:GOTO 2565

2410 J=J+1:ON KEYIN GOSUB 2600,2640:POP CH:IF CH=0 THEN 2380
2430 IF CH=13 THEN P." ":NE=1:GOTO 2565
REM IF decimal pt HIT
2450 IF CH=3 THEN DP=1:GOTO 2370
2455 IF CH=4 THEN NE=NE*(-1):GOTO 2490
2460 IF CH<48 .OR. CH>57 THEN 2370
2470 USN=ABS(USN):IF DP=0 THEN USN=USN*10 + (CH - 48):GOTO 2490
2480 USN=USN + ((CH - 48) / (10*DP)):DP=DP*10
2490 USN=NE*USN:PUSH USN
REM determine-LCD-digits()
2510 GOSUB 1380:GOSUB 1430
REM at least 1 valid digit has been entered.
2550 INFLAG = 1:IF KEYIN = 0 THEN P. CR,">>",USN,
2560 GOTO 2370
2565 POP J,I:RETURN

REM (KEYBEEP) - CHANGES K
REM           - USES APORT2,LGT
```

```
2570 PUSH I:XBY(APORT2)=1:FOR I=1 TO 50:NEXT I
2572 XBY(APORT2)=0:POP I:RETURN

REM (GETKEYBOARD) - CHANGES
REM              - USES

2600 PUSH GET:RETURN

REM (GETKEYPAD) - CHANGES CH
REM            - USES    CPORT2

2640 CH=XBY(CPORT2):IF (CH .AND. OFH) = OFH THEN CH=0:PUSH CH:RETURN
2641 GOSUB 2650
2642 CH2=CH:CH=XBY(CPORT2):IF (CH.AND.OFH)=OFH THEN CH=0:PUSH CH:RETURN
2643 GOSUB 2650:IF (CH<>CH2) THEN CH=0:PUSH CH:RETURN
2644 GOSUB 2570
2645 CH2=XBY(CPORT2):IF (CH2<>15) THEN 2645
2646 PUSH CH:RETURN

REM (READPAD) - CHANGES CH
REM           - USES CPORT2,KPD,W,Q,I

2650 PUSH W, Q, I:W = 0:Q = 10H:I=3
2660 IF( (CH .AND. 1)= 1) THEN W=W+1:CH=INT(CH/2):GOTO 2660
2670 XBY(CPORT2)=Q:CH=XBY(CPORT2)
2680 IF((CH .AND. OFH)<>OFH) THEN Q=Q*2:I=I-1:GOTO 2670
2685 XBY(CPORT2)=0
2690 CH= KPD(W*4+I):POP I,Q,W:RETURN

REM (GETPSWD) - CHANGES W, Q
REM           - USES CH, $(0), KEYIN

2730 W = 1: Q = 1:P." ":P. " ": P. "Enter Password (12357) >>",
2750 IF Q = 1350 THEN PUSH 0: RETURN
2760 ON KEYIN GOSUB 2600,2640:POP CH:IF CH = 0 THEN Q = Q + 1: GOTO 2750
2770 IF CH = ASC($(0),W) THEN W=W+1 ELSE W=1
2780 IF W < 6 THEN 2750
REM correct password entered.
2800 PUSH 1: RETURN REM (SYSTEMSTATUS) - CHANGES
REM                - USES SDAY, SMTH, SYR, SHRS, HRSH, HRSL, NRRECS,
REM                       WRAPS, MAXRECS, NXTREC 2840 P."            SYSTEM STATUS":P. " "
2850 P."Started:",SDAY,"/",SMTH,"/",SYR,"at",SHRS,":00 hours"
2860 P."Hours of operation:",((256*HRSH) + HRSL)/60
2870 P."Records stored in file:", NRRECS
2880 P."Records lost due to lack of storage:",WRAPS*MAXRECS+NXTREC-NRRECS
2890 P." "
2900 RETURN REM (SYSTEMSTATUS - FOR PRINTER) - CHANGES
REM                              - USES SDAY, SMTH, SYR, SHRS, HRSH, HRSL,
REM                                     NRRECS, WRAPS, MAXRECS, NXTREC 2910 P.#"            SYSTEM STATUS":P.# " "
2912 P.#"Started:",SDAY,"/",SMTH,"/",SYR,"at",SHRS,":00 hours"
2914 P.#"Hours of operation:",((256*HRSH) + HRSL)/60
2916 P.#"Records stored in file:", NRRECS
2918 P.#"Records lost due to lack of storage:",WRAPS*MAXRECS+NXTREC-NRRECS
2920 P.#" "
2922 RETURN
```

```
REM (GETUSERDATA) - CHANGES KIND
REM              - USES SDAY, SMTH, SYR, SHRS, USN, SD, GAIN

2940 P. U.(0)," ":$(1)=" Main Menu":PUSH 10:GOSUB 1410
2960 GOSUB 2840:GOSUB 2360
REM get-user-input()
3090 IF USN = TMOUT .OR. USN=NODIGIT THEN 2940
3100 IF USN = 13 THEN RETURN
3130 IF USN < 1 .OR. USN > 12 THEN P. "OUT OF RANGE": GOTO 2940
3140 USN = USN - 1
3150 ON USN GOSUB 3210,3420,3500,3570,3200,3660,3612,3470,3540,3180,3190,34
00
3170 GOSUB 400:GOTO 2940

REM (PRINTTOSCRN) - CHANGES POUT
REM               - USES TERM . JUMPS TO PRINT

3180 POUT=TERM:GOTO 4900

REM (PRINTTOPRNT) - CHANGES POUT
REM               - USES LPRTER . JUMPS TO BAUD

3190 POUT=LPRTER:BAUD 4800:GOTO 4900

REM (RESETRECORDS) - CHANGES
REM                - USES

3200 $(1)="Reset Records?":PUSH 14:GOSUB 1410:GOSUB 2360
3202 IF (USN=TMOUT.OR.USN=NODIGIT) THEN RETURN
3203 IF USN<>0 THEN RETURN
3204 NXTREC=0:NRRECS=0:WRAPS=0:RETURN

REM (GETDATE) - CHANGES SYR, SMTH, SDAY
REM           - USES USN

3210 $(1)="Year=":PUSH 5:GOSUB 1410:PUSH SYR:GOSUB 1750
3230 IF USN = TMOUT THEN RETURN
3240 IF USN = NODIGIT THEN 3270
3250 IF USN < 1989 THEN GOSUB 1640: GOTO 3210
3260 SYR=USN
3270 $(1)="Month=":PUSH 6:GOSUB 1410:PUSH SMTH:GOSUB 1750
3290 IF USN = TMOUT THEN RETURN
3300 IF USN = NODIGIT THEN 3330
3310 IF USN<1 .OR. USN>12 THEN GOSUB 1640:GOTO 3270
3320 SMTH = USN
3330 $(1)="Day=":PUSH 4:GOSUB 1410:PUSH SDAY:GOSUB 1750
3360 IF (USN=TMOUT .OR. USN=NODIGIT) THEN RETURN
3370 IF USN<1 .OR. USN>31 THEN GOSUB 1640: GOTO 3330
3380 SDAY=USN:RETURN

REM (ADD/REMOVE RAW DATA) - CHANGES RAW
REM                       - USES

3400 $(1)="Raw Data?":PUSH 9:GOSUB 1410:GOSUB 2360
3402 IF (USN=0) THEN RAW=1 ELSE RAW=0
3404 RETURN REM (GETTIME) - CHANGES SHRS
REM           - USES USN
3420 $(1)="Hour=":PUSH 5:GOSUB 1410:PUSH SHRS:GOSUB 1750
3440 IF (USN=TMOUT .OR. USN=NODIGIT) THEN RETURN
```

```
3450 IF USN<0 .OR. USN>23 THEN GOSUB 1640: GOTO 3420
3460 SHRS=USN:RETURN

REM (CHANGE DISPLAYED VALUES) - CHANGES DISP
REM                           - USES

3470 $(1)="Display=":PUSH 8:GOSUB 1410:PUSH DISP:GOSUB 1750
3471 IF(USN>=1.AND.USN<=9) THEN DISP=USN
3472 RETURN

REM (STOP) - CHANGES USN
REM        - USES

3500 $(1)="Program Stopped":PUSH 15:GOSUB 1410
3510 STOP
3530 USN=0:RETURN

REM (CHANGEUNITS) - CHANGES
REM               - USES

3540 $(1)="Units=":PUSH 6:GOSUB 1410:GOSUB 1740:GOSUB 2360
3542 IF (USN>=1 .AND. USN<=5) THEN DISPU=USN
3544 RETURN

REM (RESETSYS) - CHANGES
REM            - USES USN

3570 $(1)="Reset System?":PUSH 13:GOSUB 1410:GOSUB 2360
3590 IF (USN<>0) THEN RETURN
3595 $(1)=" Please Wait...":PUSH 15:GOSUB 1410
3600 FOR I=MTOP+4 TO MEMORY:XBY(I)=0:NEXT I:GOTO 90

REM (CHGSAMPLE) - CHANGES I, USN
REM             - USES SMALLINC, LARGEINC, SDMAX, DELTA, MAXRECS

3612 PUSH I
3616 $(1)=" Sampling Menu":PUSH 14:GOSUB 1410
3618 IF( MAXRECS <>0 ) THEN 3629
3619 I=SDMAX:ON SDMAX GOTO 3623,3622,3621,3620
3620 GOSUB 3641:I=I-1
3621 GOSUB 3641:I=I-1
3622 GOSUB 3641:I=I-1
3623 GOSUB 3641:I=I-1
REM get-user-input()
REM if time-out occurs then continue
3629 GOSUB 2360:IF USN = TMOUT THEN POP I:RETURN
3630 IF USN = NODIGIT THEN 3616
3632 IF USN = 9 THEN POP I:RETURN
3633 IF USN>3 .AND. USN<(5+SDMAX) .AND. MAXRECS=0 THEN GOSUB 4550:GOTO 3636
3634 USN=USN-1:IF USN < 0 .OR. USN > 2 THEN 3616
3635 ON USN GOSUB 3654,3644,3637
3636 IF USN = TMOUT THEN POP I:RETURN ELSE 3616

REM (CHGDELTA) - CHANGES DELTA
REM            - USES USN

3637 $(1)="Delta=":PUSH 6:GOSUB 1410:PUSH DELTA:GOSUB 1750
3638 IF (USN=TMOUT .OR. USN=NODIGIT) THEN RETURN
3639 IF USN>.2 THEN GOSUB 1640: GOTO 3637
3640 DELTA = USN:RETURN
```

```
REM (WINCHGP) - CHANGES
REM           - USES SDMAX, I, MAXPTS

3641 P. TAB(9),SDMAX-I+4,". # of Samples in Averages for S/D ",I+1,"..",
3642 P.MAXPTS(I):RETURN REM (CHGLINC) - CHANGES LARGEINC
REM           - USES USN
REM  LARGEINC is the number of cycles required in a FOR-NEXT loop to
REM  obtain the desired delay in seconds. Each cycle requires ~0.00154
REM  seconds.

3644 S(1)="Delay=":PUSH 6:GOSUB 1410:PUSH LARGEINC*0.00154:GOSUB 1750
3646 IF (USN=TMOUT .OR. USN=NODIGIT) THEN RETURN
3648 IF USN<0 THEN GOSUB 1640: GOTO 3644
3649 LARGEINC = USN/0.00154:RETURN

REM (CHGSINC) - CHANGES SMALLINC
REM           - USES USN

3654 S(1)="Space=":PUSH 6:GOSUB 1410:PUSH SMALLINC:GOSUB 1750
3656 IF (USN=TMOUT .OR. USN=NODIGIT) THEN RETURN
3658 IF (USN<0.OR.USN>0.5) THEN GOSUB 1640: GOTO 3654
3659 SMALLINC = USN:RETURN REM (CHGEQPARMS) - CHANGES USN
REM              - USES SD, K1, K2, K3, KS1, KS2, KS3, ALPHA, GAIN,
REM                SL, SU, SSL, SSU REM clear-LCD-display(), get-user-input()
3660 S(1)="Calculation Menu":PUSH 16:GOSUB 1410:GOSUB 2360
REM if time-out occurs then continue
3830 IF USN = TMOUT THEN RETURN
3840 IF USN = NODIGIT THEN 3660
3850 IF USN = 8 THEN RETURN
3860 IF USN<1 .OR. USN>7 THEN 3660
3870 USN = USN - 1
3880 ON USN GOSUB 4410,3940,4200,4120,4480,3902,4300
3890 IF USN = TMOUT THEN RETURN
3900 GOTO 3660

REM (READ CONTROL LIMITS - EXTINCTION) - CHANGES SU, SL
REM                                    - USES USN, SD

3902 S(1)="SL=":PUSH 3:GOSUB 1410:PUSH SL(SD):GOSUB 1750
3904 IF USN = TMOUT THEN RETURN
3906 IF USN = NODIGIT THEN 3912
3908 IF ABS(USN) > 100000 THEN GOSUB 1640:GOTO 3902
3910 SL(SD)=USN
3912 S(1)="SU=":PUSH 3:GOSUB 1410:PUSH SU(SD):GOSUB 1750
3914 IF USN = TMOUT THEN RETURN
3916 IF USN = NODIGIT THEN RETURN
3918 IF ABS(USN) > 100000 THEN GOSUB 1640:GOTO 3912
3920 SU(SD)=USN:RETURN

REM (READ CALIBRATION CONSTANTS - EXTINCTION) - CHANGES K1, K2, K3
REM                                           - USES USN, SD

3940 S(1)="K1=":PUSH 3:GOSUB 1410:PUSH K1(SD):GOSUB 1750
3960 IF USN = TMOUT THEN RETURN
3970 IF USN = NODIGIT THEN 4000
3980 IF ABS(USN) > 100000 THEN GOSUB 1640:GOTO 3940
3990 K1(SD)=USN
```

```
4000 S(1)="K2=":PUSH 3:GOSUB 1410:PUSH K2(SD):GOSUB 1750
4010 IF USN = TMOUT THEN RETURN
4020 IF USN = NODIGIT THEN 4050
4030 IF ABS(USN) > 100000 THEN GOSUB 1640:GOTO 4000
4040 K2(SD)=USN
4050 S(1)="K3=":PUSH 3:GOSUB 1410:PUSH K3(SD):GOSUB 1750
4060 IF (USN=TMOUT .OR. USN=NODIGIT) THEN RETURN
4070 IF ABS(USN) > 100000 THEN GOSUB 1640:GOTO 4050
4080 K3(SD)=USN:RETURN

REM (READ ALPHAS - DIRECT) - CHANGES ALPHA()
REM                        - USES USN, KIND

4120 PUSH I:I=2
4130 S(1)="ALPHA=":PUSH 6:GOSUB 1410:PUSH ALPHA(SD*7+I-2):GOSUB 1750
4135 IF USN = TMOUT THEN 4180
4140 IF USN = NODIGIT THEN 4170
4150 IF USN<=0 THEN GOSUB 1640:GOTO 4130
4160 ALPHA(SD*7+I-2)=USN
4170 I=I+1:IF I<=8 THEN 4130
4180 POP I:RETURN

REM (READ CALIBRATION CONSTANTS - SCATTERED) - CHANGES KS1, KS2, KS3
REM                                           - USES USN, SD

4200 S(1)="KS1=":PUSH 4:GOSUB 1410:PUSH KS1(SD):GOSUB 1750
4205 IF USN = TMOUT THEN RETURN
4210 IF USN = NODIGIT THEN 4225
4215 IF ABS(USN) > 100000 THEN GOSUB 1640:GOTO 4200
4220 KS1(SD)=USN
4225 S(1)="KS2=":PUSH 4:GOSUB 1410:PUSH KS2(SD):GOSUB 1750
4230 IF USN = TMOUT THEN RETURN
4235 IF USN = NODIGIT THEN 4250
4240 IF ABS(USN) > 100000 THEN GOSUB 1640:GOTO 4225
4245 KS2(SD)=USN
4250 S(1)="KS3=":PUSH 4:GOSUB 1410:PUSH KS3(SD):GOSUB 1750
4255 IF (USN=TMOUT .OR. USN=NODIGIT) THEN RETURN
4260 IF ABS(USN) > 100000 THEN GOSUB 1640:GOTO 4250
4265 KS3(SD)=USN:RETURN

REM (READ CONTROL LIMITS - SCATTERED) - CHANGES SU, SL
REM                                    - USES USN, SD

4300 S(1)="SSL=":PUSH 4:GOSUB 1410:PUSH SSL(SD):GOSUB 1750
4302 IF USN = TMOUT THEN RETURN
4304 IF USN = NODIGIT THEN 4310
4306 IF ABS(USN) > 100000 THEN GOSUB 1640:GOTO 4300
4308 SSL(SD)=USN
4310 S(1)="SSU=":PUSH 4:GOSUB 1410:PUSH SSU(SD):GOSUB 1750
4312 IF USN = TMOUT THEN RETURN
4314 IF USN = NODIGIT THEN RETURN
4316 IF ABS(USN) > 100000 THEN GOSUB 1640:GOTO 4310
4318 SSU(SD)=USN:RETURN

REM (CHGSD) - CHANGES SD
REM         - USES USN, SDMAX

4410 S(1)="S/D=":PUSH 4:GOSUB 1410:PUSH SD+1:GOSUB 1750
4420 IF (USN=TMOUT .OR. USN=NODIGIT) THEN RETURN
4440 IF USN>0 .AND. USN<(SDMAX+2)THEN SD=USN-1:RETURN
4450 GOSUB 1640:GOTO 4410

REM (CHGGAIN) - CHANGES GAIN
REM           - USES SD, USN
```

```
4480 $(1)="GAIN=":PUSH 5:GOSUB 1410:PUSH GAIN(SD):GOSUB 1750
4490 IF (USN=TMOUT .OR. USN=NODIGIT) THEN RETURN
4500 IF USN<1 .OR. USN>8 THEN GOSUB 1640: GOTO 4480
4510 GAIN(SD) = USN:RETURN

REM (READWINDOWSZ) - CHANGES MAXPTS, I
REM                - USES USN, SDMAX

4550 I=4+SDMAX-USN:PUSH I
4555 POPI:PUSHI:$(1)="Sample=":PUSH 7:GOSUB 1410:PUSH MAXPTS(I):GOSUB 1750

4565 IF (USN=TMOUT .OR. USN=NODIGIT) THEN RETURN
4570 IF USN<1 .OR. USN>200 THEN GOSUB 1640: GOTO 4555
4580 POP I:MAXPTS(I)=USN:RETURN

REM (PRINTRECS) - CHANGES NRPRT, NREC, LINE, J, I, W
REM             - USES USN, NRRECS, SMEAN, DMEAN, SD, HRSL, HRSH, PLINES
REM                    CH, KEYIN

REM print-operational-contants()
4900 GOSUB 5240:$(1)="#Records?":PUSH 9:GOSUB 1410
REM get-user-input()
4920 GOSUB 2360:IF USN=TMOUT .OR. USN=NODIGIT THEN RETURN
4930 IF USN = 0 THEN RETURN
4940 NRPRT = USN:IF NRPRT > NRRECS THEN NRPRT = NRRECS
4950 IF NRPRT = 0 THEN RETURN
REM get-user-input()
5010 $(1)="1=Start, 0=Stop":PUSH 15:GOSUB 1410
5015 GOSUB 2360:IF USN <> 1 THEN RETURN 5020 PUSH SMEAN,DMEAN,J,W,HRSL,HRSH,PF:W=SD:I=0:NREC = NXTREC - 1:LINE = 1
5025 DBY(1CH)=HRSL:DBY(1DH)=HRSH
5030 FOR J=1 TO NRRECS
REM put-header-line()
5050 IF LINE = 1 THEN GOSUB 5440
5060 IF NREC < 0 THEN NREC = MAXRECS
5070 PUSH NREC
REM read-record(NREC)- is it ours?
5090 GOSUB 1940:IF(W <> SD) THEN 5160
5100 IF(DBY(1DH)*255+DBY(1CH)-(HRSH*255+HRSL) < 60)THEN 5105
5101 P."No Change For More Than 1 Hour"
5105 DBY(1CH)=HRSL:DBY(1DH)=HRSH
REM perform-calculations()
5110 GOSUB 2080
REM display-record()
5130 GOSUB 5550:NRPRT=NRPRT-1:LINE=LINE+1:IF LINE>PLINES THEN LINE = 1
REM read-input-once()
5160 GOSUB 2640:POP CH:IF CH = 48 .OR. GET = 48 THEN 5195
5180 NREC = NREC - 1:IF NRPRT = 0 THEN 5190
5185 NEXT J
5190 SD=W:POP PF,HRSH,HRSL,W,J,DMEAN,SMEAN:$(1)="Hit key to cont."
5191 PUSH 16:GOSUB 1410
5193 ON KEYIN GOSUB 2600,2640:POP CH:IF CH=0 THEN 5193 ELSE RETURN
5195 P. "Stopped due to user intervention.":GOTO 5190

REM (PRTOPDATA) - CHANGES
REM             - USES SD, K1, K2, K3, KA, KB, KC, KD, KE, GAIN, POUT

REM call print-system-status()
5240 PUSH J:IF POUT = LPRTER THEN 5330
5250 GOSUB 2840:P." "
5260 P."Current Equation Parameters are:"
5270 P."K1=",K1(SD),",   K2=",K2(SD),",   K3=",K3(SD)
5275 P."KS1=",KS1(SD),",  KS2=",KS2(SD),",  KS3=",KS3(SD)
```

```
5280 FOR J=2 TO 8
5290 P."Alpha for Gain Level ",J,":",ALPHA(SD*7+J-2) : NEXT J
5300 P."Current Gain Level =",GAIN(SD),",   S/D Set =",SD+1
5310 P." "
5320 POP J:RETURN
5330 GOSUB 2910:P.#" "
5340 P.#"Current Equation Parameters are:"
5350 P.#"K1=",K1(SD),",   K2=",K2(SD),",   K3=",K3(SD)
5355 P.#"KS1=",KS1(SD),",   KS2=",KS2(SD),",   KS3=",KS3(SD)
5360 FOR J=2 TO 8
5370 P.#"Alpha for Gain Level ",J,":",ALPHA(SD*7+J-2) : NEXT J
5380 P.#"Current Gain Level =",GAIN(SD),",   S/D Set =",SD+1
5390 P.#" "
5400 POP J:RETURN

REM (PUTHDR) - CHANGES
REM           - USES POUT

5440 IF POUT = LPRTER THEN 5480
5450 P." Day/Hr        S/D     Gain    Scattered                Extinction"
5460 P."                Set             Susp. Solids/NTU        Susp. Solids/JTU"
5470 P." ":RETURN
5480 P.# PAGEFWD
5490 P.#" Day/Hr        S/D     Gain    Scattered                Extinction"
5500 P.#"                Set             Susp. Solids/NTU        Susp. Solids/JTU"
5510 P." ":RETURN

REM (PRTREC) - CHANGES
REM          - USES POUT, HRSH,  HRSL, SD, GAIN, RCAL

5550 IF POUT = LPRTER THEN 5610
5560 P. U.(###.###), (256*HRSH + HRSL)/1440,
5570 P. U.(#), TAB(13),SD+1,TAB(19),GAIN(SD),
5580 IF RSCAL>1.0 THEN P. U.(######.##), ELSE P. U.(#.######),
5590 P. TAB(26),RSCAL,TAB(40),:IF DISPU=5 THEN P. " N",
5592 GOSUB 5670
5594 IF RCAL>1.0 THEN P. U.(######.##), ELSE P. U.(#.######),
5596 P. TAB(49),RCAL,TAB(63),:IF DISPU=5 THEN P. " J",
5598 GOSUB 5670:P. " ":IF PF=1 THEN P. "   ** POWER INTERRUPTION **"
5600 RETURN
5610 P.# U.(###.###), (256*HRSH + HRSL)/1440,
5620 P.# U.(#), TAB(13),SD+1,TAB(19),GAIN(SD),
5630 IF RSCAL>1.0 THEN P.# U.(######.##), ELSE P.# U.(#.######),
5640 P.# TAB(26),RSCAL,TAB(40),:IF DISPU=5 THEN P.# " N",
5642 GOSUB 5680
5644 IF RCAL>1.0 THEN P.# U.(######.##), ELSE P.# U.(#.######),
5646 P.# TAB(49),RCAL,TAB(63),:IF DISPU=5 THEN P.# " J",
5648 GOSUB 5680:P.# " ":IF PF=1 THEN P.# "   ** POWER INTERRUPTION **"
5650 RETURN

REM (PRINT UNITS TO SCREEN) - CHANGES
REM                         - USES

5670 ON. (DISPU-1) GOTO 5671,5672,5673,5674,5675
5671 P. "mg/L",:RETURN
5672 P. " g/L",:RETURN
5673 P. " ppm",:RETURN
5674 P. "   %",:RETURN
5675 P. "TU",:RETURN

REM (PRINT UNITS TO PRINTER) - CHANGES
REM                          - USES
```

```
5680 ON (DISPU-1) GOTO 5681,5682,5683,5684,5685
5681 P.# "mg/L",:RETURN
5682 P.# " g/L",:RETURN
5683 P.# " ppm",:RETURN
5684 P.# "    %",:RETURN
5685 P.# "TU",:RETURN

REM (INIT) - CHANGES EVERTHING!

REM default start date: 1st May 1988
5840 SDAY=1:SMTH=7:SYR=1989:PASSWD=0:USN=0:INFLAG=0:TMOUT=-1:NODIGIT=-2
5850 SD=0:HRSL=0:HRSH=0:SHRS=0:HOUR=60:KEYIN=0:CH=0:DP=0:DISP=1:NE=1
5860 I=0:J=0:W=0:Q=0:TERM=0:LPRTER=1:POUT=TERM:B=0:LCDNUM=0:NUM=0:E=0
5865 CH2=0:DISPU=1:PF=0:RAW=0:LARGEINC=0:SMALLINC=0
5885 FOR I=0 TO 15: READ KPD(I): NEXT I
5890 DATA 48,49,50,51,52,53,54,55,56,57,1,2,3,4,5,13
5910 RESTORE
5930 PORTA=0F000H: PORTB=0F100H: PORTC=0F200H
REM
REM output,output,output
REM
5970 XBY(PORTC)=0:SDMAX=0:TMNEX=2
5980 APORT2=0EF00H: BPORT2=0EF01H: CPORT2=0EF02H: CTRLREG2 = 0EF03H
REM
REM output,output,output
REM
6020 XBY(CTRLREG2)=81H:AVGS=0: AVGD=0:DELTA=.05: OLDD=1: OLDS=1
6025 AVGDN=0:AVGDFF=0:AVGS1=0:AVGS0=0
6030 DMEAN = 0: SMEAN=0: TM=0: TMD = 0: TMS = 0
6040 FOR I=0 TO SDMAX:GAIN(I)=1
6041 SU(I)=1000: SL(I)=0:DB=0:SB=0:SSU(I)=1000:SSL(I)=0
6042 K1(I)=2:K2(I)=0.3:K3(I)=0:KS1(I)=1:KS2(I)=1:KS3(I)=0
6043 ALPHA(I*7)=10:ALPHA(I*7+1)=100:ALPHA(I*7+2)=1000:ALPHA(I*7+3)=10000
6044 ALPHA(I*7+4)=1:ALPHA(I*7+5)=1:ALPHA(I*7+6)=1
6050 WR(I)=0:MAXPTS(I)=5:NEXT I
6070 RCAL=0:NRPRT=0:LINE=1:PLINES=50:NREC=0:TCAL=0:RSCAL=0:TSCAL=0
6090 BESTI = 0: BESTRD = (128**2) + 1: RD = 0:ALPH=1:RS=0
REM set password
6110 $(0) = "12357":DAD = 0: SAD = 0
6120 ADADDR(0)=0D000H: ADADDR(1)=0D002H:ADADDR(2)=0D004H: ADADDR(3)=0D006H
6130 ADADDR(4)=0D001H: ADADDR(5)=0D003H:ADADDR(6)=0D005H: ADADDR(7)=0D007H
6200 AMTMEM=0:MAXRECS=0:NXTREC=0:RECSIZ=15:NRRECS=0:MEMSTRT=MTOP+4

6210 NXTBITE=0:POSN=0:WRAPS=0:MEMORY=32767:MEMMAX=MEMORY-285

6220 FOR I=0 TO SDMAX:WINST(I)=MEMSTRT:MEMSTRT=MEMSTRT+MAXPTS(I)*13:NEXT I
6230 AMTMEM=MEMMAX-MEMSTRT:MAXRECS=INT(AMTMEM/RECSIZ)
6250 NXTBITE = MEMSTRT:RETURN
```

I claim:
1. A turbidity meter comprising:
(a) a light source, and a lens for focusing light from the source into a beam;
(b) a first light detector producing an output signal responsive to the intensity of light incident thereon; and
(c) at least one second light detector producing an output signal responsive to the intensity of light incident thereon; said turbidity meter further comprising:
(d) means supporting said first and second light detectors in defined positions relative to the light source in a fluid under test such that said beam is directed through said fluid towards said first light detector, and each said second light detector is positioned to detect light scattered by said fluid at a predetermined angle to said beam;
(e) means to determine when the amplitude of at least one of the output signals obtained lies within a given range;
(f) means responsive to said determining means to select at least one parameter selected from the intensity of the light source and the effective sensitivity of at least one of the detectors, so that the output signal of at least one of said detectors falls within said range; and
(g) signal selection means, responsive to the selection of said at least one parameter, to select an output signal falling within said range; and

(h) weighting means to weight the selected signal in accordance with the at least one selected parameter and the identity of the signal.

2. A turbidity meter according to claim 1, wherein the light source is monochromatic, and the detectors have a spectral response substantially restricted to light of the wavelength of the source.

3. A turbidity meter according to claim 1, wherein the light source is a light emitting diode, and the detectors are semiconductor photosensors having a spectral response matching the spectral characteristics of the source.

4. A turbidity meter according to claim 1, including means to inhibit deposition of material on the source or detectors such as to obstruct the passage of light therefrom or thereto.

5. A turbidity meter according to claim 4, wherein the means to prevent deposition comprises a source of pressurized fluid compatible with the fluid under test, and means to discharge the compatible fluid in a curtain-like flow over portions of the source and detectors through which light passes, such that a moving body of the compatible fluid prevents direct contact of the fluid under test with said portions.

6. A turbidity meter according to claim 5, wherein the discharge means includes flow forming chambers having outlets positioned adjacent a substantial portion of the periphery of a source or detectors with each said outlet to discharge the compatible fluid in a generally laminar flow across said portion.

7. A turbidity meter according to claim 1, wherein one parameter changed by the means responsive to the determining means is the sensitivity of the first light detector.

8. A turbidity meter according to claim 1, wherein said signal selection means is configured to select one of a turbidimetric signal produced by the first light detector, and a nephelometric signal produced by a second light detector.

9. A turbidity meter according to claim 1, wherein said signal selection means is configured to select a turbidimetric signal produced by the first light detector if said at least one parameter can be adjusted so that the detector output falls within said range, and otherwise to select a nephelometric signal produced by a second light detector.

10. A turbidity meter according to claim 1, wherein the means of subparagraphs (e), (f) and (g) are implemented by a microcontroller, a non-volatile memory controlled by the microcontroller is provided to store successive values of said weighted output signals, and data output means are associated with the controller to output said values for monitoring and control purposes.

11. A turbidity meter comprising:
(a) an enclosed light source, and a lens for focusing light from the source into an externally directed beam;
(b) at least one light detector having a lens and producing an output signal responsive to the intensity of external light incident thereon through the lens;
(c) means supporting the light source and said at least one light detector in defined relative positions in a fluid under test such that such beam is directed through the lens of the light source into said fluid, and each light detector is positioned to detect light from said beam which enters that detector from the fluid through its lens after propagation through said fluid;
(d) means processing output signals of said at least one detector to provide a signal indicative of the turbidity of the fluid; and
(e) means to prevent deposition of material from the fluid upon the lenses;
wherein said means to prevent deposition upon the lenses comprises a source of pressurized fluid compatible with that under test, a flow forming chamber adjacent each lens and conduits from said source to each said flow forming chamber, each flow forming chamber having an exit orifice partially surrounding the periphery of a surface of its associated lens nearest the fluid under test, whereby a curtain-like flow of said compatible fluid is set up over that surface of the associated lens.

12. A turbidity meter according to claim 11, wherein the light source and light detectors are semiconductor devices packaged with integral lenses.

13. A turbidity meter according to claim 11, wherein each light source and detector is housed in a bore in a mounting assembly with its lens substantially flush with one end of the bore at the bottom of a slot defined by structure at that end of the mounting assembly, the flow forming chamber being located within one end of the slot and having an opening facing an opposite open end of the slot across the lens.

14. A turbidity meter according to claim 13, wherein the flow forming chamber extends from a second bore in said mounting block to said opening, the second bore being connected to the source of pressurized fluid, and the chamber being shaped to form fluid from said bore into said curtain-like flow.

15. A turbidity meter according to claim 11, including means to verify the presence of pressurized fluid from said source of pressurized fluid.

* * * * *